(12) United States Patent
Colinge et al.

(10) Patent No.: US 6,996,474 B1
(45) Date of Patent: Feb. 7, 2006

(54) AUTOMATED METHOD FOR IDENTIFYING RELATED BIOMOLECULAR SEQUENCES

(75) Inventors: Jacques Colinge, Neydens (FR); Rob Hooft Van Huijsduijnen, Geneva (CH)

(73) Assignee: Applied Research Systems ARS Holding N.V., Curacao (NL)

( * ) Notice: Subject to any disclaimer, the term of this patent is extended or adjusted under 35 U.S.C. 154(b) by 167 days.

(21) Appl. No.: 10/148,124

(22) PCT Filed: Nov. 16, 2000

(86) PCT No.: PCT/IB00/01676

§ 371 (c)(1),
(2), (4) Date: Dec. 5, 2002

(87) PCT Pub. No.: WO01/38568

PCT Pub. Date: May 31, 2001

(51) Int. Cl.
*G06F 17/00* (2006.01)
(52) U.S. Cl. .......................................... 702/19; 702/20
(58) Field of Classification Search ................. 702/19, 702/20
See application file for complete search history.

(56) References Cited

U.S. PATENT DOCUMENTS

| 5,598,350 A | 1/1997 | Kawanishi et al. ............ 702/20 |
| 5,701,256 A | 12/1997 | Marr et al. ..................... 702/20 |
| 5,843,732 A | 12/1998 | Davis et al. ................... 436/94 |
| 5,873,052 A | 2/1999 | Sharaf ........................... 702/20 |

OTHER PUBLICATIONS

Abstract for EP 0646883, Hitachi Device Eng, et al, Apr. 5, 1995, obtained from the Internet Oct. 13, 1999 at http://ep.espacenet.com/.
Abstract for WO 9714106, Terrapin Tech Inc., Apr. 17, 1997, obtained from the Internet Oct. 13, 1999 at http://ep.espacenet.com/.
Abstract for EP 0829810, Kureha Chemical Inc. Co. Ltd (JP), Mar. 18, 1998, obtained from the Internet Oct. 13, 1999 at http://ep.espacenet.com/.
Abstract for WO 9826407, Incyte Pharma Inc., Jun. 18, 1998, obtained from the Internet Oct. 13, 1999 at http://ep.espacenet.com/.
Abstract for WO 9847086, Alpha Gene Inc., Oct. 22, 1998, obtained from the Internet Oct. 13, 1999 at http://ep.espacenet.com/.
Abstract for WO 9846998, Clark Robert D, Oct. 22, 1998, obtained from the Internet Oct. 13, 1999 at http://ep.espacenet.com/.
Abstract for WO 9847087, Glaxo Group Ltd., et al., Oct. 22, 1998, obtained from the Internet Oct. 13, 1999 at http://ep.espacenet.com/.

Abstract for DE 19745665, Deutsches Krebsforsch, May 12, 1999, obtained from the Internet Oct. 13, 1999 at http://ep.espacenet.com/.
Altschul et al, "Basic Local Alignment Search Tool", *J. Mol. Biol.*, 215: 403-410 (1990).
Altschul et al, "Gapped BLAST and PSI-BLAST: A New Generation of Protein Database Search Programs", *Oxford University Press*, 3389-3402 (1997).
Altschul et al, "Issues in Searching Molecular Sequence Databases", *Nat Genet.* 6(2): 119-129 (1994).
Altschul et al, "Local Alignment Statistics", *Methods in Enzymology*, 266: 460-480 (1996).
Andrade et al, "Bioinformatics: From Genome Data to Biological Knowledge", *Curr Opin Biotechnol*, 8(6): 675-83 (1997), Abstract Only.
Botstein et al, "Yeast as a Model Organism", *Science*, 277:1259-1260 (1997).
C Elegans: Sequence to Biology, "Genome Sequence of the Nematode C. Elegans: A Platform for Investigating Biology", *Science*, 282: 2012-2018 (1998).
Chervitz et al, "Comparison of the Complete Protein Sets of Worm and Yeast: Orthology and Divergence", *Science*, 282:2022-2028 (1998).
Copley et al, "Protein Families in Multicellular Organisms", *Curr Opin Struct Biol*, 9(3): 408-15 (1999). Abstract only.
Goffeau et al, "Life with 6000 Genes", *Science*, 274:546-567 (1996).
Hanke et al, "Associative Database of Protein Sequences", *Bioinformatics*, 15(9): 741-748 (1999).
Karlin et al, "Applications and Statistics for Multiple High-Scoring Segments in Molecular Sequences", *Proc. Natl. Acad. Sci. USA*, 90:5873-5877 (1993).

(Continued)

*Primary Examiner*—James Martinell
(74) *Attorney, Agent, or Firm*—Browdy and Neimark, P.L.L.C.

(57) ABSTRACT

The invention relate to an automated method for identifying related biomolecular sequences having defined features of interest from databases, the databases comprising at least a first and a second set of sequences, each set being derived from a different type of organism, comprising the steps of: a) establishing from the first set of sequences a non-redundant list of query sequences having the defined features of interest (first family members), using a database search program; b) performing sequence alignments with the first family members in a second set of sequences derived from a second type of organism, using a database search program and a preset similarity threshold, giving a list of second family members: c) establishing a two dimensional matrix displaying the first and second family members and their respective similarity values resulting from step (b), optionally displaying only those second family members having similarity values exceeding a preset threshold value; d) selecting from the matrix those pairs of first and second family members for which the similarity values are the best among all of the alignments that involve one of the two pair's members (orthologs).

12 Claims, 2 Drawing Sheets

OTHER PUBLICATIONS

Koonin et al, "Beyond Complete Genomes: From Sequence to Structure and Function", *Curr Opin Struct Biol,* 8(3): 355-63 (1998), Abstract Only.

Lipman et al, "Rapid and Sensitive Protein Similarity Searches", *Research Article,* 1435-1441 (1985).

Luster et al, "Role of the Monocyte Chemoattractant Protein and Eotaxin Subfamily of Chemokines in Allergic Inflammation", *J. of Leukocyte Biology,* 62: 620-633 (1997).

Muda et al, "Identification of the Human YVH1 Protein-tyrosine Phosphatase Orthologue Reveals a Novel Zinc Binding Domain Essential for in Vivo Foundation", *J. of Bio. Chem.,* 274(34): 23991-23995 (1999).

Nicholas et al, "A Tutorial on Searching Sequence Databases and Sequence Scoring Methods, Developed by the Biomedical Supercomputing Initiative of the Pittsburgh Supercomputing Center, An NIH Supported Resource Center", (1998).

Pearson et al, "Comparison of DNA Sequences with Protein Sequences", *Genomics,* 46: 24-36 (1997).

Pearson et al, "Improved Tools for Biological Sequence Comparison", *Proc. Natl. Acad. Sci. USA,* 85: 2444-2448 (1988).

Pearson W, "Rapid and Sensitive Sequence Comparison with FASTP and FASTA", *Methods in Enzymology,* 183: 63-98 (1990).

Rouze et al, "Genome Annotation: Which Tools Do We Have For It?", *Curr Opin Plant Biol,* 2(2): 90-5 (1999), Abstract Only.

Smith et al, "Identification of Common Molecular Subsequences", *J. Mol. Biol,* 147: 195-197 (1980).

Van Huijsduijnen, "Protein Tyrosine Phosphatases: Counting the Trees in the Forest", *Gene,* 225: 1-8 (1998).

Van Vactor, "Genetic Analysis of Protein Tyrosine Phosphatases", *Current Opinion In Genetics & Development,* 8: 112-126 (1998).

Zhang et al, "A Greedy Algorithm for Allgning DNA Sequences", *J. of Computational Biology,* 7(1/2): 203-214 (2000).

Fig. 1a

Fig. 1b

AUTOMATED METHOD FOR IDENTIFYING RELATED BIOMOLECULAR SEQUENCES

FIELD OF THE INVENTION

The present invention relates to an automated method for identifying related biomolecular sequences having defined features of interest from databases, the databases comprising at least a first and a second set of sequences, each set being derived from a different type of organism.

BACKGROUND OF THE INVENTION

Within the past few years, the amount of biological information available in databases and accessible via the World Wide Web is increasing at a fast pace. The biggest part of this information is made up of DNA sequences derived from more and more efficient DNA sequencing methods. However, DNA sequencing methods only provide raw data, among which the scientist then has to find what is important. The important parts may be coding sequences, splice sites, regulatory sequences like promoters and terminators, polyadenylation sites etc. Selecting the sequence of interest from the wealth of sequence data is essential, since the "real" experiments at the laboratory bench performed to analyze the molecules containing the sequence and/or their products require a big effort in terms of time and resources. Experiments based on the molecules taken from the database aim at elucidating structure and function of these biomolecules. These experiments may then lead to finding new drugs or drug targets, for example.

Therefore, the sequence data present in a database has to be carefully analyzed and evaluated, in order to sort out the sequences of interest to the particular research project.

Being interested in a certain protein or a protein family (i.e. related proteins sharing common motifs, which may be domains or certain amino acid residues or patterns of residues), the researcher is often faced with the problem that only a member in one specific type of organism has been characterized. It is known that the sequences of homologous proteins can diverge greatly in different organisms, even though the structure or function change little. Thus, much can be inferred about an uncharacterized protein when significant sequence similarity is detected with a well-studied protein. Therefore, a database search, i.e. a sequence comparison or alignment, is performed in order to find other family members and/or related molecules in other types of organisms. Homologous family members in different organisms are called orthologs.

Databases like Swissprot, GenBank or the EMBL (European Molecular Biology Laboratory) Data Library are large sequence archives containing large amounts of sequence data. The databases contain sets of sequences stemming from different organisms. In these databases, searches for orthologs can be performed starting from a query sequence which is aligned with the sequences in a database, the target sequences. A score, defining the similarity, is computed for each alignment, and the query-target pairs are reported to the user. The score or similarity value can be set to a certain threshold or "cut-off value", so that only those pairs having a similarity exceeding the threshold are reported to the user.

Different programs or algorithms have been developed to perform database searches. The Smith-Waterman algorithm (1) rigorously compares the query sequence with every target sequence in the database. This algorithm requires time proportional to the product of the lengths of sequences compared. Without special-purpose hardware or massively parallel machines the time required by the Smith-Waterman algorithm is usually too slow for most users. Much quicker programs for database searches use heuristics to speed up the alignment procedure. The most commonly used programs of this kind are called BLAST and FASTA, both concentrating the alignment on the sequence regions most likely to be related. Rapid exact-mach procedures first identify promising regions, and only then is the Smith-Waterman method applied.

Newly identified DNA sequences can be classified using known nucleic acid or amino acid sequence motifs that indicate particular structural or functional elements. The motifs can then be used for predicting the function of a newly identified sequence.

More sensitive sequence comparisons can be carried out using sequence families, preferably conserving certain critical residues and motifs. All the members of the family or putative family members are used for the search. Using multiple sequence comparisons, gene functions may be revealed that are not clear from simple sequence homologies.

In order to find orthologous proteins, Chervitz et al. (2) performed an exhaustive comparison of complete protein sets of the nematode worm *Caenorhabditis elegans* and the budding yeast *Saccharomyces cerevisiae*. Both the genome of the yeast and the genome of the nematode *C. elegans* had been sequenced in totality before (3, 4).

In order to find orthologous relationships, Chervitz et al. performed a reciprocal Washington University (WU)-BLAST analysis (described in 5, 6 and 7). They compared the predicted yeast proteins (6217 ORFs) against all the predicted proteins of the worm (19 099 ORFs) and vice versa, i.e. they performed a reciprocal sequence comparison. Good alignments were detected and grouped together. The groups were then ordered according to their similarity and displayed as multiple sequence alignments, rooted cluster dendrograms and unrooted trees.

This analysis showed that for a substantial fraction of the yeast and worm genes, orthologous relationships were identifiable. This approach of identifying orthologous relationships in different species serves at finding protein functions and activities in newly sequenced genomes.

Reciprocal sequence comparisons are therefore a powerful tool for helping researchers identify their potential target in the database and then design experiments to the specific molecule identified.

One of the difficulties in analyzing the results of database searches as outlined above is the amount of data output obtained by the search. The output has to be carefully evaluated in order to select the significant data from the "background".

Another difficulty is the ambiguity of the results presented in dendrograms or trees. Pairs of orthologs are not evident, if detectable at all.

A further critical item is the reliability of the analysis. Researchers have to be sure that the sequences they found are unequivocally and truly orthologous pairs, i.e. that they have actually or at least very likely found sequences coding for proteins or domains having a certain activity. The success in finding orthologs using these kinds of database searches is the more likely, the closer evolutionary linked the organisms compared are.

However, most sequence information available today is derived either from mammalian species or from very simple life forms. This situation will be even more lopsided when the full human genomic sequence is known.

The explanation for this situation is that simple organisms have relatively small genomes which are accessible to manipulation, whereas mammalian (human) genetic data are essential as the immediate starting point for the development of pharmaceutical derivatives. But in order to infer the function of a mammalian gene from the analysis of a related gene (an ortholog) of worm or a fly, for instance, by deleting the orthologous gene, one has to be reasonably certain about the evolutionary relationship between those two genes.

The avalanche of sequencing data has increased the number of mammalian genes whose function can potentially be studied in lower organisms, but due to the lack of sequences from evolutionary "intermediate" species it is usually impossible to trace genes all the way through evolutionary trees. This problem is especially prominent for gene families with numerous genes such as kinases, phosphatases and receptors.

As mentioned above, among the multicellular organisms, the genome of the nematode worm *Caenorhabditis elegans* (*C. elegans*) has been sequenced in totality (4). Although medical and pharmacological interests tend to focus on mammalian genes, only simple life forms like the nematode allow rapid genetic manipulation and functional analysis. A prerequisite for the meaningful extrapolation of gene functional studies from invertebrates to man is that the pairs of related genes, the orthologs, under study are really related, i.e. unambiguously linked.

SUMMARY OF THE INVENTION

Therefore, it is an object of the present invention to provide a reliable method for identifying related biomolecular sequences having defined features of interest, i.e. orthologs, in databases. It is a further object of the invention to simplify the evaluation of results obtained in database searches aiming at identifying related biomolecular sequences. The method should be applicable even to the alignment of sequences derived from evolutionary distant species.

The invention relates to a reliable method for identifying orthologous polypeptide or polynucleotide sequences in databases. The method can be used even with sequences derived from evolutionary distant species.

This problem is solved by an automated method for identifying related biomolecular sequences having defined features of interest from databases, the databases comprising at least a first and a second set of sequences, each set being derived from a different type of organism, comprising the steps of:
a) establishing from the first set of sequences a non-redundant list of query sequences having the defined features of interest (first family members), using a database search program;
b) performing sequence alignments with the first family members in a second set of sequences derived from a second type of organism, using a database search program and a preset similarity threshold, giving a list of second family members;
c) establishing a two dimensional matrix displaying the first and second family members and their respective similarity values resulting from step (b), optionally displaying only those second family members having similarity values exceeding a preset threshold value;
d) selecting from the matrix those pairs of first and second family members for which the similarity values are the best among all of the alignments that involve one of the two pair's members (orthologs).

This method presents an important improvement of the multiple alignment methods known in the art.

BRIEF DESCRIPTION OF THE DRAWINGS FIGURE LEGEND AND TABLES

Figure 1A:
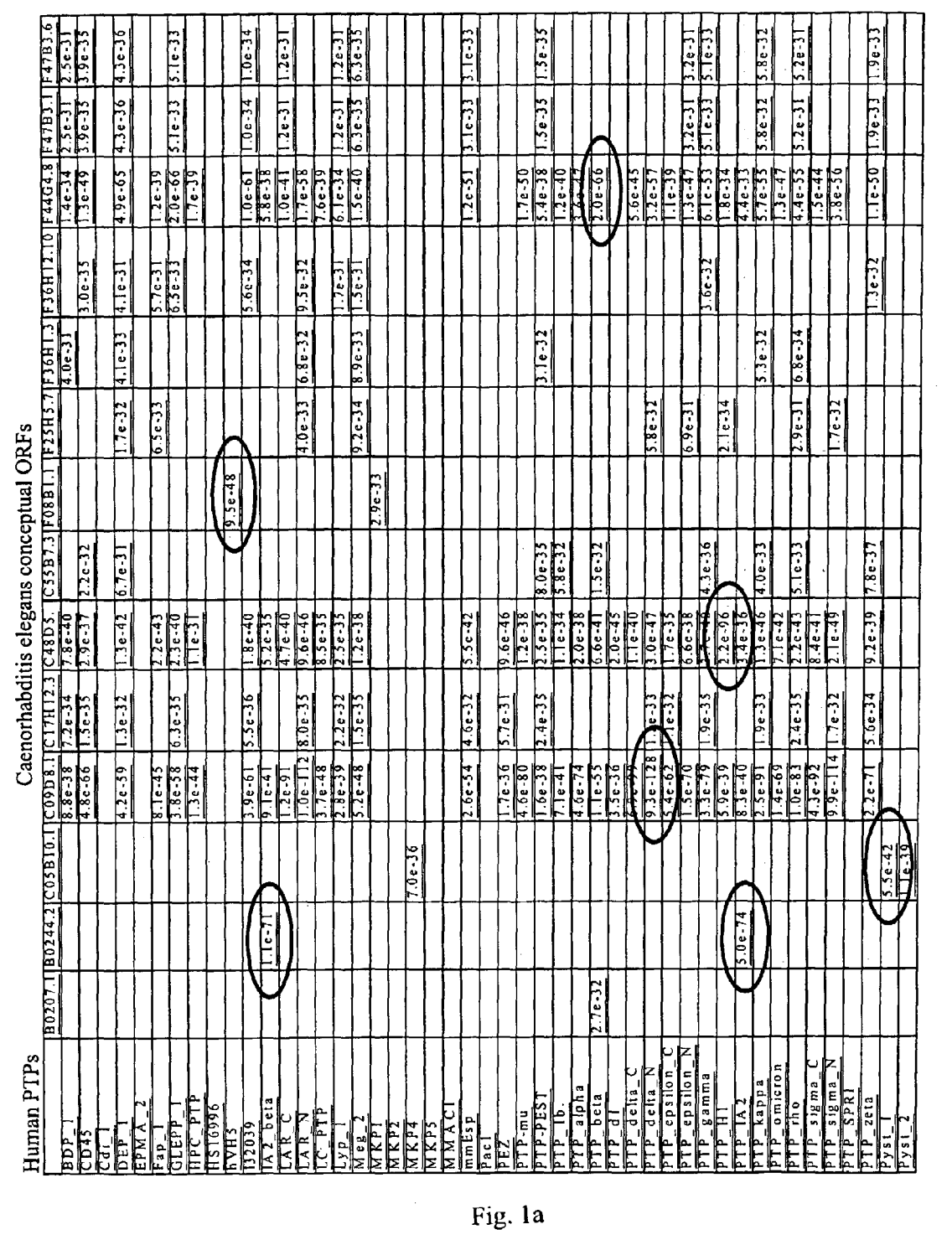
Figure 1B:
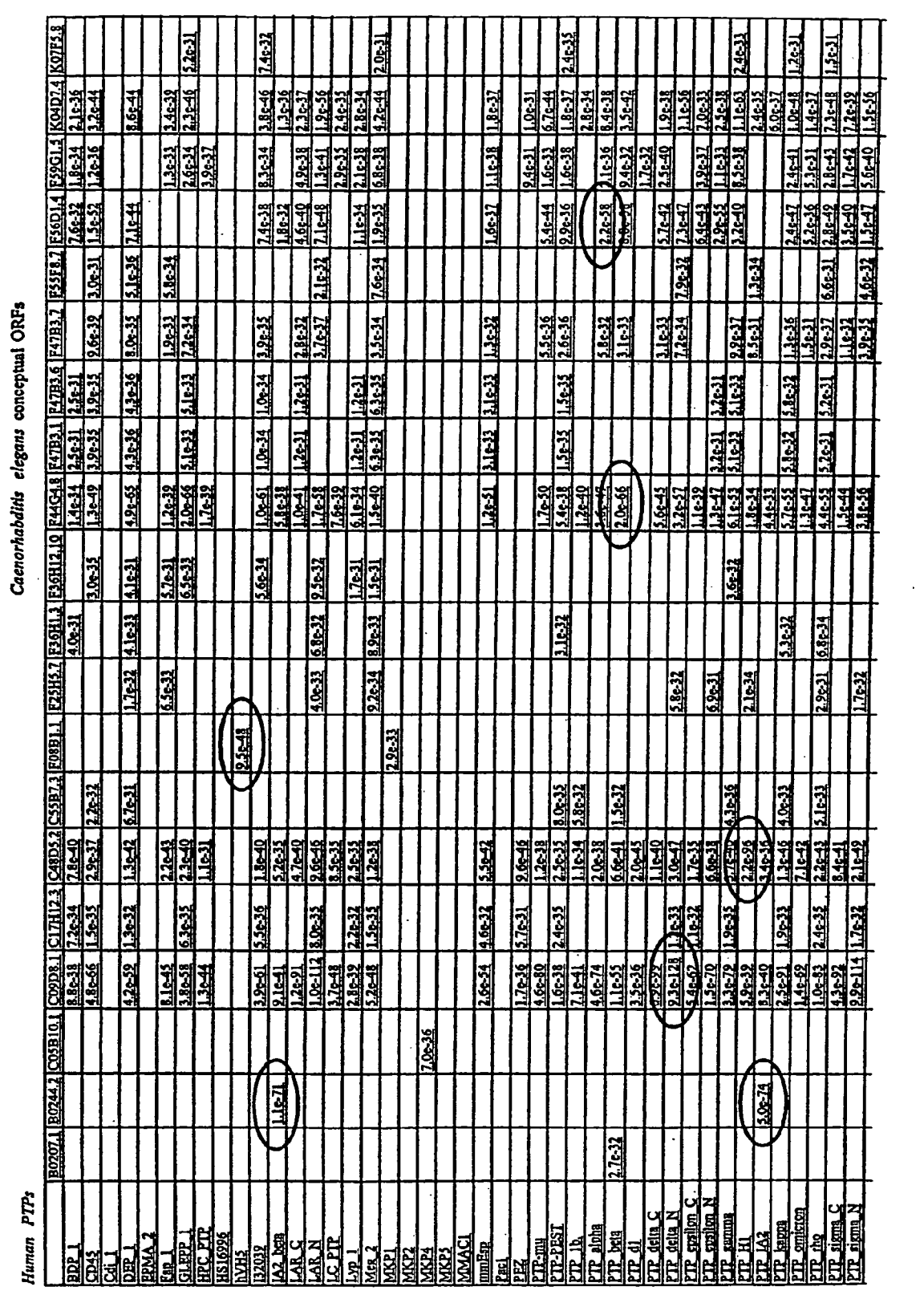

FIG. 1a illustrates an enlarged portion of FIG. 1b, which illustrates a BLAST analysis according to the invention between human Protein Tyrosine Phosphatases (PTPs) catalytic domains and *C. elegans* conceptual ORFs. Only ORFs with PTP BLAST $p<10^{-30}$ values are displayed. The circles indicate intersections of the "best ortholog" pairs.

Table I:

Human-Worm PTP Orthologs.

The list was compiled from data shown in FIG. 1, and taken from gene pairs with the highest similarity for both axes (except for Meg-2 and YVH-1; see example 1). Previously identified *C. elegans* PTP orthologs are named.

Table II:

Other (non-*C. elegans*) PTP orthologs identified by a BLAST analysis according to the invention in the EMBL database. Using the same approach as shown in FIG. 1 and Table I, a list was compiled of human PTP orthologs in other species, based on EMBL data. Synonyms for the orthologs are given where different from human. Mm: *Mus musculus*; Rn: *Rattus norvegicus*; Rr: *Rattus rattus*; Hf: *Heterodontus francisi*; Gg: *Gallus gallus*; Oc: *Oryctolagus cuniculus*; Xl: *Xenopus laevis*; Ps: *Pisum sativum*.

DESCRIPTION OF THE INVENTION

Step (a): First, a list of sequences representing a family of sequences as, for example, a gene family, is compiled from the database. The sequences extracted from the database may be further modified, for example only selecting a certain piece of sequence. Such a piece of sequence may contain an exon, coding for a domain specific for a certain family of proteins, for instance. The list of first family members has to be non-redundant. This is essential in order to minimize the total amount of alignments, therefore substantially speeding up the method according to the invention as compared to alignment methods known in the art. Non-redundancy may be obtained by first assembling the sequences and then comparing them among each other, eliminating any identical sequences. The list of first family members is derived from one specific organism, i.e. taken from one set of sequences comprising the sequences derived from a certain organism. The set of sequences may be contained in one or more databases. The family members are identified by their common features of interest, like sequence motifs representing domains of polypeptides, for example. The family members can be taken from the database(s) by methods known in the art (8). In addition to this, databases are already available containing gene families, like Prosite, for example.

Step (b): Then, with each of these family members, called first family members, a comparison in a set of sequences derived from another organism is performed. The set of sequences may be contained in one or more databases. This comparison is symmetrical. Step (b) leads to a list of sequences similar to the first family members, called second family members. The degree of similarity can be tuned by choosing an adequate threshold value. Establishment of the adequate threshold value is well within the knowledge of the skilled person.

Step (c): In order to be able to select the highly significant, i.e. "unequivocal" orthologs, a two-dimensional similarity matrix is established. The size of the matrix can be adjusted to the individual needs by choosing a certain threshold or cut-off value for the similarity. The more stringent the threshold value for similarity is set, the smaller the matrix will be. The optionally preset threshold value also determines the calculation time. The matrix need not be visually displayed, but can be virtually established by the computer. Then, it may be very large. If visually displayed, only those family members are displayed in the matrix whose similarity values are better than, i.e. exceeding a preset threshold or cut-off value. The threshold value is chosen to indicate a highly significant similarity. As mentioned above, it can be preset by the researcher according to his needs. The more stringent the threshold value is, the less "hits" or family members will be shown. Establishment of the threshold value is well within the knowledge of the skilled person. Selecting a stringent threshold value will allow to build up a clearly laid out similarity matrix. A special display of the results is used according to the invention. The similarity matrix shows the results in a way the unequivocal family members can be readily and automatically detected and selected (see step (d)). The similarity matrix simultaneously displays the first family members and their matching second family members as well as their respective similarity values resulting from the sequence alignments performed in the comparison step carried out before, i.e. in step (b).

Step (d): The last step of the method according to the invention consists of actually selecting the pairs of orthologs. Those pairs are selected having the similarity values representing the highest similarity among all of the alignments involving one of the two members of the pairs. The unambiguous orthologs are readily detectable by just choosing the similarity value maximal in horizontal and vertical direction. First, the values in a specific row containing the alignments of a first family member are screened. The highest value is chosen. In order to be sure about the orthology, this value also has to be the best in the respective column. If the similarity value is best both in the row and column, it defines a pair of orthologs. In step (d), not only "the best" or "highest" value can be selected, but also more than one value, if not only one value reflects a high degree of similarity. For example, if there are three values reflecting a very high degree of similarity, three pairs of very likely orthologs have been identified. The results may then be compiled to a list of orthologous pairs.

The process according to the invention thus combines a maximum of reliability of the results with a high speed of the search. Speed is accelerated compared to conventional methods because the sequences started with are already carefully selected. The list of first family members is reduced, since it contains in a non-redundant way, i.e. only once, the sequences known to share specific features of interest. Since most databases have duplicate or even multiple entries for the same sequence, redundancies have to be removed. This can be done by comparing all sequences of the family, which were found, then comparing them and deleting the identical ones.

Another advantage of the method according to the invention is due to the presentation of the results in a matrix as outlined above. It does not rely on visual inspection of evolutionary trees, but automatically selects and optionally visually displays the best- matching pair of orthologs, i.e. the one or ones having the highest similarity to each other.

Therefore, using the method according to the invention, one-to-one pairs of unambiguous orthologs can be identified, even if the sets of sequences the search is performed in are derived from evolutionary distant types of organisms. The whole process can be automated and carried out on a computer. The basic parameters like the features defining the sequences of interest and the threshold values for the database searches are set up before, according to the respective goal or need of the researcher.

Using this novel approach, it was possible to identify unequivocal one-to-one orthologous pairs which failed to be identified as such before in the known databases, using conventional methods as rooted cluster dendrograms and unrooted trees. The ease and reliability of the method of the invention will be appreciated by all those interested in related or homologous sequences and who use bioinformatics for choosing the molecules which are further analyzed in the laboratory afterwards.

The term "type of organism" should be understood as species or any other organism or self-replicating agent/entity being distinguishable from another organism or self- replicating agent/entity.

As already mentioned above, the "best value" should be understood as also meaning the best values, i.e. more than one can be chosen.

The databases used according to the invention can be e.g. the EMBL database, Swissprot, GenBank, the NCBI databases etc. The term database may comprise any collection of data containing one or more sets of sequences derived from one or more of different types of organisms.

Preferably, the first set of sequences, from which the list of first family members is established in step (a), comprises different databases, all derived from the same type of organism. By assembling information from different databases available, one can make sure to begin with a family of sequences as complete as possible.

The different databases used for the sequence alignments in step (a) can be selected from the group consisting of amino acid databases, nucleic acid databases, genomic sequence databases and expressed sequence tag (EST) databases.

In a preferred embodiment of the invention, the method according to the invention comprises additionally, or instead of steps (c) and (d), the steps of:
e) performing sequence alignments with the second family members identified in step (b) in one or more databases containing sequences derived from the type of organism the first family members were taken;
f) comparing the sequences resulting from the alignments of step (e) with the list of first family members established in step (a) and selecting those sequences additionally found in step (e);
g) adding to the list of first family members the sequences selected in step (f).

If steps (e), (f) and (g) are carried out instead of steps (c) and (d), it is possible to identify further first family members being related to the second family members, which had not identified before in step (a).

If steps (e) to (f) are carried out in addition to steps (a) to (d), they may be considered as confirmation or completion steps further enhancing the reliability of the method according to the invention. A further search is performed in a database or several databases containing sequences the first family was taken from. In this series of alignments, the second family members are used as query sequences. Either all of the second family members are used, or only those being one of a pair identified in step (d).

The databases used for the sequence alignments of step (e) may be selected from the group consisting of amino acid databases, nucleic acid databases, genomic sequence databases and expressed sequence tag (EST) databases. The use of different databases again serves to assemble as much information as possible, resulting in highly reliable analyses.

Advantageously, the steps of the method according to the invention are reiterated one or more times. This leads to more and more complete lists of first and second family members as well as to more and more complete lists of one-to-one orthologs.

In a further advantageous embodiment the cells of the table are color coded according to their similarity values. This renders visual inspection of the matrix especially easy. The matrix thus gains a very clear layout, allowing for a quick evaluation of the results. For example, similarity values representing a low similarity can be designed in dark colors like blue or black, the color becoming lighter the higher the similarity is. The highest values can be laid out in cells having signal colors like red or yellow.

For large tables not suited to visual inspection, color codes are not needed. In this case, the computer may automatically output the pairs of orthologs in a simple list or the like.

In a highly preferred embodiment the matrix is displayed in a format able to link each cell of the matrix to information related to the content of the cell. A suitable format for this is the HTML format, for example. It is further preferred that cells of the matrix contain designations of the family members, and the designations of the family members are hyperlinked to their respective sequences present in the database. The cells of the matrix containing the similarity values may further be hyperlinked to their respective sequence alignments.

This allows the matrix to be very clearly laid out. Family members can easily be represented by certain designations, like names, numbers, letter codes or combinations thereof, and by clicking on them, the sequences are automatically called up from the database. When the similarity values are hyperlinked to the searches performed before, by clicking on the values, the search can be called up and analyzed without the data interfering with the clarity of the similarity matrix itself. This kind of associative display renders the evaluation of the results much quicker and easier, relieving the scientist from having to analyze large amount of datasets. By reducing the amount of data, i.e. only showing the essential information, the risk of overlooking important results is further diminished.

Another advantage of this is that the data can be analyzed off-line, saving time and online costs.

In a further preferred embodiment, the sets of sequences are derived from different types of organisms having a high evolutionary distance from each other. The evolutionary distance can be calculated with statistical methods. A known way to determine evolutionary distances is based on the scoring matrix PAM.

The sets of sequences may be derived from mammals and invertebrates, respectively. They may even be derived from species as far apart as human beings and *Caenorhabditis elegans*.

The method the inventors of the present invention have developed is especially suited for searches for homologous pairs among species having a high evolutionary distance. The special sequence of searches performed in the steps according to the invention together with the selection of maximal similarity values renders the probability of finding true orthologs high enough to be sure about the homology even when the similarity is weak or when a gene family has "fanned out". As can be taken from the annexed examples, the inventive system allows for identification of orthologous pairs that could not be found by traditional comparisons, like evolutionary trees and the like.

In further preferred embodiments, the biomolecular sequences are selected from the group consisting of nucleic acid sequences and amino acid sequences. The databases may contain genomic or expressed nucleic acid sequences, according to the needs or interest of the respective research project and/or availability.

The features of interest may define a specific class of protein or a specific domain or motif of a protein. Sequences coding for proteins define products that can potentially serve as drugs or drug targets and are therefore of a high interest to researchers aiming at finding new drugs.

If the search is done with a specific domain of a protein, for example a catalytic domain of an enzyme, which is likely to be conserved among different species, the speed of the search can be further increased, since the speed depends on the length of the query sequences used for the database searches.

The features of interest being contained in the query sequences may define the protein tyrosine phosphatase (PTP) gene family. Protein tyrosine phosphatases are enzymes of high interest, since protein tyrosine phosphorylation and dephosphorylation are key switches in many important eukaryotic cellular signaling pathways.

The known database search programs used in the method according to the invention can be any of the known suitable programs. Programs based on heuristics are especially preferred, like FASTA or the BLAST algorithm. Most preferably, the BLAST program is used, since it is very fast and broadly used throughout the scientific community.

In programs as, for example in the BLAST program, similarities are scored as p-values or probability values. The lower the p-value is, the higher the similarity is, and vice versa. The p-value threshold can be user-defined. It is preset before starting the automated method, so that only those pairs scored with a p-value exceeding a certain threshold, i.e. lower than the preset cut-off value, are displayed to the user.

The threshold values depend on the gene family which is analyzed. Threshold values typically lie in the range of $10^{-10}$ to 0.

The invention is further described in the following examples in combination with the annexed figure. The examples are not intended to limit the scope of the invention, but further illustrate the method according to the invention.

EXAMPLES

Materials and Methods:

A Perl script was written to automatically perform a series of BLAST (Washington University BLAST2, which is a specific implementation of the original BLAST algorithm (5) searches. The blasts were carried out against the EMBL, Swissprot or "WormPep" (available online from The Wellcome Trust Sanger Institute: The *C. elegans* Protein Database) databases. The blasts were run locally on a Silicon Graphics Inc. Origin 200 (4 processors) workstation with an IRIX operating system. The time required for the above blasts was approximately 4–5 h, 15 min, and 5 min respectively. The output was parsed into a set of indexed files. A web interface was generated by another Perl (CGI) script that reproduced the blast-data in a table-form based on a user-defined cut-off probability value. The row- and column headers in the able hyperlinked to the database entries, the p-values in the Table itself hyperlinked to the BLAST sequence alignment.

Example 1

First, a complete, non-redundant list of all human members of the gene family (PTPs) was established (8). Briefly, the full set of database entries with similarities to the PTP-PEST catalytic domain were identified in a BLAST search and their sequences downloaded. These sequences were then compared one by one to the others in the set for having identical catalytic domains. Thus, redundancies in the form of duplicate database entries or alternative splice forms were eliminated.

The members of this list were then sequentially "blasted" against the full set of conceptual *C. elegans* ORFs. The result of these BLASTs are shown in FIG. 1. The output for this Figure was generated according to a user-defined BLAST threshold ($p<10^{-30}$). The data is displayed in HTML such that the gene and ORF names hyperlink to their sequences and the result cells to their BLAST sequence alignment. One practical advantage of this approach is that all BLAST results are stored locally so that data can be analyzed "off-line". More importantly, data is analyzed by locating cells that represent the best similarity values both horizontally and vertically (marked by circles in FIG. 1). The highlighting of the best matches can of course also be done automatically by the computer.

One can identify potential ortholog gene pairs that would not be obvious from traditional comparisons. For example, for many human PTPs, ORF C09D8.1 (fourth column in FIG. 1) has the best sequence similarity among all worm PTPs, yet the reverse BLAST with C09D8.1 indicates that only PTP-delta N ($p=9.10^{-128}$) is the best ortholog candidate. Eleven examples of such "most likely worm orthologs" have been found. They were also listed in Table I. Only four of these had been described previously, and all these four were also identified by the method according to the invention, namely PTP-IA2 4, SHP1/2 4, MMAC-1 5 and PTP-alpha 6. YVH1 was only recently described (9), and was not included in our original list of human PTPs (8).

This analysis according to the invention is especially useful when the similarity between the human gene and its ortholog is weak, or when a gene family has "fanned out", as appears to be the case for C09D8.

A phylogenetic tree of all the genes shown in FIG. 1, calculated with PileUp software (GCG version 10.0) failed to identify these relationships (data not shown).

This result shows that the method according to the invention reveals new possibilities screening for families of related sequences in databases.

Example 2

Another analysis according to the invention was performed in which the set of human PTPs was compared to the full EMBL database. Although the resulting dataset was much larger than the one reproduced in FIG. 1, it was possible to extract from this the PTP ortholog list shown in Table II.

There is no fundamental obstacle to analyzing full genomes using the method according to the invention. Larger datasets lead to linear increases in calculation times, in contrast to combinatorial algorithms such as those needed to completely solve a "travelling salesman" type of problem. Given a current hardware setup and 150,000 human ORFs, we estimate that a full man-worm genome comparison would require approximately nine days of calculation to produce a complete list of most likely ortholog pairs.

TABLE I

| | Human PTPs | *C. elegans* | EMBL Acc. | Name |
|---|---|---|---|---|
| 1 | HVH5 | F08B1.1 | U23178 | Not described |
| 2 | Meg_2 | F38A3 | Z49938 | Not described |
| 3 | MMAC_1 | T07A9.6 | AF036706 | DAF-18 |
| 4 | PTP_IA2, IA2beta | B0244.2 | U28971 | CEL-STYX |
| 5 | PTP-alpha | F56D1.4 | U39997 | CLR-1 |
| 6 | PTPbeta | F44G4.8 | Z54218 | Not described |
| 7 | PTPdelta | C09D8.1 | Z46811 | Not described |
| 8 | PTPH1 | C48D5.2 | Z36237 | Not described |
| 9 | Pyst 1 | C05B10.1 | AF036685 | Not described |
| 10 | SHP_1/2 | F59G1.5 | U23178 | PTP-2 |
| 11 | U14603 | T19D2.2 | AF063401 | Not described |
| 12 | YVH-1 | C24F3.2 | AL022716 | Not named |

TABLE II

| H. sapiens | Accession # | Other Sp. | Synonym |
|---|---|---|---|
| BDP-1 | U35124 | Mm | |
| CD45 | RNLCAR/LCA11 | Rn | |
| " | MMLY5A | Mm | Ly5 |
| " | GDPTYPHLA | Gd | PTP lambda |
| " | GGPTP | Gg | PTPlambda |
| " | HF 34750 | Hf | |
| " | AF 024438 | Xl | |
| Fap1 | MMPZPTP/PTPN13 | Mm | |
| GLEPP1 | GG U65891 | Gg | PTP CRYP-2 |
| " | OC09490 | Oc | |
| " | MM37465/66/67 | Mm | |
| " | RRBEM1 | Rr | BSM-1 |
| HPC-PTP | F09723 | Rn | |
| " | MMPHPRSL/MMPTPBR7 | Mm | PTP SL |
| HS16996 | AF 013144 | Rn | MAPK-PTP (cpg 21) |
| hVH-5 | MMTTPIGN | Mm | |
| I32039 | AF 063249 | Rn | |
| IA2beta | RNPTPASE | Rn | |
| " | MMU57345 | Mm | |
| LAR | MMLAR_N | Mm | |
| " | RNLARPTPB/LAR1/LAR2 | Rn | |
| Lyp-1 | MMPROTyPH | Mm | |
| Meg-2 | XLTYPHA | Xl | PTPXIO |
| " | AF 013490 | Mm | |
| MKP-1 | RNRNADSP | Rn | |
| " | RR02553 | Rr | |
| " | MM3CH134 | Mm | |
| " | AF 026522 | Gg | |
| MMAC-1 | AF017185 | Rn | |
| Pac-1 | MMAPC-1 | Mm | |
| Pcz | MMPTP36 | Mm | |
| PTP alpha | GGPTPA | Gg | |
| " | RNPTPLRP | Rn | |
| " | MMRPA01 | Mm | |
| PTP Gamma | GG U38349 | Gg | |
| PTP omicron | RRU66566 | Rr | RPTP psi |
| PTP omicron C | D88187/MM55057 | Mm | |
| PTP PEST | RRRKPTP | Rr | |
| " | MMPTPPES | Mm | |
| PTP SPRI | AF077000 | Rn | PTP TD14 |
| " | PSA 5589 | Ps | |
| PTP zeta | GG PHOPHOS | Gg | |
| PTP1b | GG 46662 | Gg | CPTP1 |
| " | MM24700/MMPTPASE | Mm | MMPTPIX |
| PTP-beta | MMMRPTPB | Mm | |
| PTPd1 | MMPTPRL/RL10 | Mm | |
| " | RN 17971 | Rn | |

TABLE II-continued

| H. sapiens | Accession # | Other Sp. | Synonym |
|---|---|---|---|
| PTPdelta_N | GGCRYP | Gg | |
| " | RRTYRPHOS | Rr | |
| " | MMMRPTPA | Mm | |
| PTP-epsilon_N | RNPTPECA | Rr | |
| " | MMPTPE | Mm | |
| PTP-IA2 | MM11812 | Mm | PTP35A |
| " | RRBEM3 | Rr | |
| " | RSPDPTPLP | R | |
| " | RN 40652/RNICCA105 | Rn | |
| PTP-Kappa | MMPTPA | Mm | |
| PTP-mu | MMRPTPU | Mm | |
| PTP-sigma | RNPTPPS | Rn | |
| Pyst-2 | RNMKPX | Rn | |
| Sap-1 | RRBEM 2 | Rr | |
| SHP-1 | MMPRTHYPHB/ MMHCPA | Mm | |
| SHP-2 | D83016 | Rn | |
| " | VRTIGG38620 | Gg | CSH-PTP2 |
| " | MMBYP/MMSHPTP2 | Mm | |
| STEP | MM28217 | Mm | |
| TC-PTP | MMPTP/MMCPTP | Mm | |
| " | RNPTP/-S | Rn | |
| U 14603 | RRPRLINP | Rr | |
| " | MM 84411 | Mm | PRL-1 |
| " | RN 07016 | Rn | |

REFERENCES

1. Smith, T. F. and Waterman, M. S. Identification of common molecular subsequences. M. S. J. Mol. Biol. 147, 195–1971 (1981).
2. Chervitz S. A., Aravind, L., Sherlock, G., Ball, C. A:, Koonin, E. V., Dwight, S. S., Harris, M. A., Dolinski, K., Mohr, S., Smith, T., Weng, S., Cherry, J. M. and Botstein, D. Comparison of the Complete Protein Sets of Worm and Yeast: Orthology and Divergence. Science 282, pp. 2022–2028 (1998).
3. The C. elegans sequencing consortium. Genome sequence of the nematode C. elegans: a platform for investigating biology. The C. elegans Sequencing Consortium. Science 282, 2012–8 (1998).
4. A. Goffeau. Life with 6000 genes. Science 274, 546 (1996).
5. Altschul, S. F., Gish, W., Miller, W., Myers, E. W. & Lipman, D. J. Basic local alignment search tool. J Mol Biol 215, 403–10 (1990).
6. Karlin, S. and Altschul, S. F., Applications and statistics for multiple high scoring segments in molecular sequences. Proc. Natl. Acad. Sci. USA 90, 5873 (1993).
7. Altschul, S. F. and Gish W. Local alignments statistics. Methods Enzymol. 266, 460 (1996).
8. Hooft van Huijsduijnen, R. Protein Tyrosine Phosphatases: Counting the Trees in the Forest. Gene 225, 1–8 (1998).
9. Muda, M., Manning, E. R., Orth, K. & Dixon, J. E. Identification of the human YVH1 protein-tyrosine phosphatase orthologue reveals a novel zinc binding domain essential for in vivo function. J Biol Chem 274, 23991–5 (1999).

What is claimed is:

1. Automated method for identifying orthologous polypeptide or polynucleotide sequences from databases, the databases comprising at least a first and a second set of sequences, each set being derived from a different species, comprising the steps of:

(a) establishing from the first set of sequences derived from a first species a non-redundant list of query sequences having common features of interest (first family members), using a database search program;

(b) performing sequence alignments with the first family members in a second set of sequences derived from a second species, using a database search program and a preset similarity threshold, giving a list of second family members and their similarity values with the first family members;

(c) establishing a two dimensional matrix displaying the first and second family members and their respective similarity values resulting from step (b), optionally displaying only those second family members having similarity values exceeding a preset threshold value;

(d) selecting from the matrix those pairs of first and second family members for which the similarity values are closest to the value zero among all of the alignments that involve one of the two pair's members (orthologs).

2. Method according to claim 1, comprising additionally the steps of:

(a) performing sequence alignments with the second family members in one or more databases containing sequences derived from the species the first family members were taken;

(b) comparing the sequences resulting from the alignments of step (e) with the list of first family members established in step (a) and selecting those sequences additionally found in step (e);

(c) adding to the list of first family members the sequences selected in step (f).

3. Method according to claim 2, wherein the method is reiterated one or more times.

4. The method according to claim 1, wherein the sets of sequences of the first and the second family members are derived from different species.

5. The method according to claim 4, wherein the sets of sequences of the first and second family members are derived from mammals and invertebrates, respectively.

6. The method according to claim 5, wherein the sets of sequences of the first and second family members are derived from human beings and *Caenorhabditis elegans*, respectively.

7. The method according to claim 1, wherein the features of interest define a specific protein, a specific domain of a protein or a protein family.

8. The method according to claim 7, wherein the features of interest define the protein tyrosine phosphatase (PTP) protein family.

9. The method according claim 1, wherein the cells of the matrix are color coded according to their similarity values.

10. The method according to claim 1, wherein the matrix is displayed in a format able to link each cell of the matrix to information related to the content of the cell.

11. The method according to claim 10, wherein cells of the matrix contain designations of the family members, and the designations of the family members are hyperlinked to their respective sequences present in the database.

12. The method according to claim 10, wherein cells of the matrix containing the similarity values are hyperlinked to their respective sequence alignments.

* * * * *